United States Patent [19]

Kaeding et al.

[11] 4,197,413
[45] Apr. 8, 1980

[54] PRODUCTION OF 3-METHYLPHENOL

[75] Inventors: Warren W. Kaeding, Westfield; Margaret M. Wu, Somerville; Lewis B. Young, Skillman; George T. Burress, Bridgewater, all of N.J.

[73] Assignee: Mobil Oil Corporation, New York, N.Y.

[21] Appl. No.: 969,628

[22] Filed: Dec. 14, 1978

[51] Int. Cl.² ............................................. C07C 37/08
[52] U.S. Cl. .................................. 568/798; 568/570; 568/768; 585/455; 585/468 R
[58] Field of Search ...................... 568/798, 768, 570; 260/671 C

[56] References Cited

U.S. PATENT DOCUMENTS

| | | | |
|---|---|---|---|
| 2,760,991 | 8/1956 | Toland, Jr. | 568/800 |
| 2,805,258 | 9/1957 | Boorman et al. | 568/752 |
| 2,862,857 | 12/1958 | Filar | 568/768 |
| 3,215,745 | 11/1965 | Frank | 568/572 |
| 3,755,483 | 8/1973 | Thomas | 260/671 |
| 3,928,469 | 11/1975 | Suda et al. | 568/768 |
| 4,098,836 | 7/1978 | Dywer | 260/668 A |

FOREIGN PATENT DOCUMENTS 754872   8/1956   United Kingdom ................... 568/798

Primary Examiner—Werren B. Lone
Attorney, Agent, or Firm—Charles A. Huggett; Ronald J. Cier

[57] ABSTRACT

A four-step method for the selective production of the 1,3-isomer of methylphenol comprising the alkylation of toluene with propylene in the presence of a specified type of zeolite alkylation catalyst followed by the selective reaction, via a specified type of shape selective zeolite, of the 1,4-isomer of the alkylation product to leave the 1,3-isomer thereof in excess of equilibrium. Subsequent oxidation and acid catalyzed rearrangement results in desirably high yield of 3-methylphenol.

16 Claims, No Drawings

PRODUCTION OF 3-METHYLPHENOL

BACKGROUND OF THE INVENTION

1. Field of the Invention

This invention is concerned with the production of aromatic alcohols, and in particular with the selective production of 3-alkylphenols and 1,3-dihydroxybenzene.

2. Description of the Prior Art

The organic compound phenol has found many important industrial and medical applications over the years. It is valuable both as an intermediate in the manufacture of other compounds and as a useful material in its own right. Modern manufacturing processes are described in detail in the monograph by A. Dierichs and R. Kubicka, *Phenole und Basen, Vorkommen und Gewinnung* (Akademie-Verlag, Berlin, 1958).

3-Methylphenol is presently used in disinfectants, fumigants, photographic developers and explosives. Its potential as a phenolic resin for adhesives and other industrial products is large, particularly in view of some of the unique characteristics of this particular derivative of phenol, e.g., it is approximately three times more reactive then the parent phenol and has increased toughness, moisture resistance and reduced brittleness, all of which are very desirable properties. However, a major drawback to widened industrial applications for this compound has been its relatively high cost of manufacture. Japanese Pat. No. 8929 (1955) to Maesawa and Kurakano describes a process for obtaining this compound from coal tar. Its preparation from toluene is disclosed by Toland in U.S. Pat. No. 2,760,991. Another process, involving oxidation of o- or p-toluic acid, is described by Kaeding et al. in *Ind. Eng. Chem.* 53, 805 (1961). However, separation of the 3-methyl compound (bp 202° C.) from the mixed product stream, a necessary step in the heretofore practiced synthetic processes, is at best a very difficult and expensive undertaking.

1,3-Dihydroxybenzene has, like phenol, found numerous uses in both the medical and industrial areas as an intermediate in the synthesis of other materials and also as a useful substance by itself. A common method for manufacturing this useful compound has been by fusing 1,3-benzenedisulfonic acid with excess sodium hydroxide.

SUMMARY OF THE INVENTION

We have now found a novel and useful route for the manufacture of both 3-alkylphenols and 1,3-dihydroxybenzene in substantially higher yields than obtained heretofore. Our discovery is basically a four step process for producing the desired hydroxylated aromatic compound from readily available raw materials such as benzene or alkylated benzene compounds. The first and second steps in the process involve the production, in high yield, of the 1,3-dialkyl isomer of the benzene compound. Steps three and four comprise the oxidation of at least one of the alkyl substituents on the benzene ring followed by acid catalyzed rearrangement to produce the desired aromatic hydroxy compound and an alkyl ketone by-product.

The general reaction scheme comprises:

Step (1)

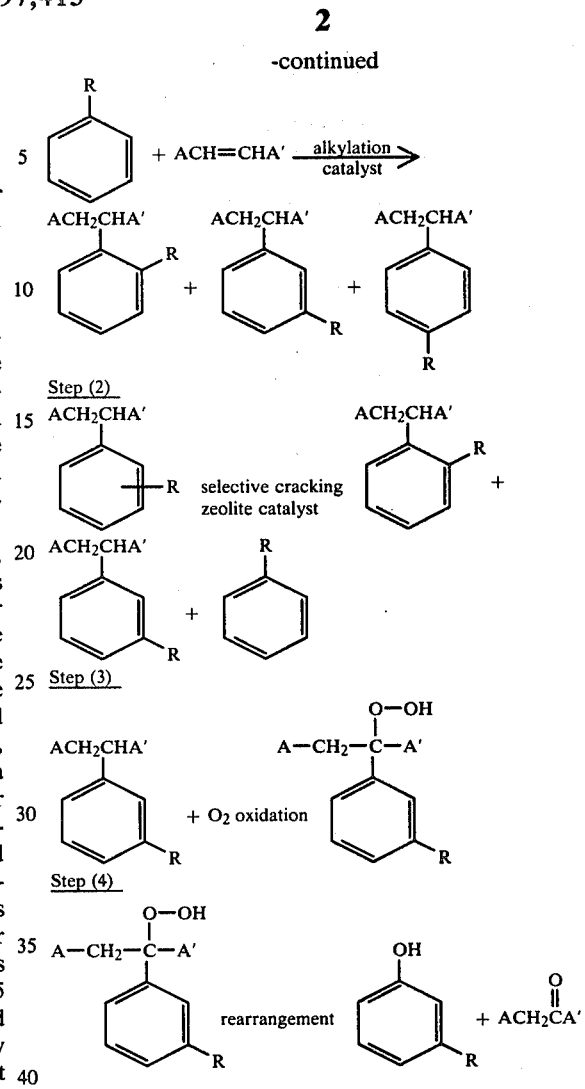

wherein:
R = alkyl
A = hydrogen or alkyl
A' = hydrogen or alkyl

The alkylation reaction, Equation (1), may be carried out in the presence of any known alkylation catalyst, many of which are conventionally classified as Lewis Acids and Bronsted Acids. When a known, conventional alkylation catalyst is utilized, the reactants are brought into contact therewith under conditions of temperature and pressure appropriate to that catalyst. In a particularly preferred embodiment, the alkylation catalyst comprises a novel type of crystalline zeolite catalyst characterized by a silica to alumina mole ratio of at least about 12 and a constraint index, as hereinafter defined, within the approximate range of 1 to 12. In such preferred embodiment, the olefin and aromatic compounds are brought into contact with the zeolite, most preferably the crystalline zeolite ZSM-5 or zeolite ZSM-12, at a temperature within the approximate range of bout 100° C. to 400° C. and a pressure of between about $10^5$ N/m$^2$ and $4 \times 10^6$ N/m$^2$, preferably at about 200° C. to 350° C.

The selective cracking step to remove the undesirable 1,4-isomer, Equation (2), is accomplished by contacting, under selective cracking conditions, the isomeric mixture resulting from the foregoing alkylation step with a specified type of shape selective crystalline zeolite catalyst having a silica to alumina ratio and constraint index as set out above, whereupon the 1,4-dialkylbenzene is selectively cracked or transalkylated to leave a product enriched in the 1,2- and 1,3-dialkyl isomers. The preferred selective cracking conditions comprise a temperature within the approximate range of about 100° C. to 500° C. and a pressure of approximately $10^4$ N/m$^2$ to $10^6$ N/m$^2$ (0.1 to 10 atmospheres). The preferred crystalline zeolite catalysts for this step are ZSM-5, ZSM-11 and ZSM-23.

The last two steps of the synthesis consist of an oxidation, Equation (3), and an acid catalyzed rearrangement, Equation (4), which are analogous to the known commercial process for the production of phenol (i.e., where R=H).

DESCRIPTION OF SPECIFIC EMBODIMENTS

To facilitate the detailed explanation and understanding of the invention, the process will be broken down to its four component steps and each will be discussed separately. It must be realized, of course, that the process of the present invention comprises the sum total of its steps and that the following separate discussions of each of these steps is merely for the sake of conveying a clear understanding of the entire process as herein disclosed.

Step 1—Alkylation of the aromatic compound

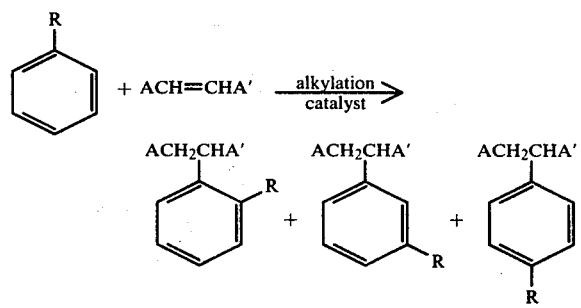

where:
R=alkyl
A=hydrogen or alkyl
A'=hydrogen or alkyl.

The alkylation reaction is carried out by contacting the aromatic and olefinic compounds with an alkylation catalyst, which may comprise any of the conventional alkylation catalysts loosely classified as Lewis and Bronsted acids. The conventional alkylation catalysts utilized herein may comprise any conventional catalyst designed to promote the alkylation of aromatic compounds with olefins. Such conventional catalysts include those which may be broadly defined as being Lewis and Bronsted acids. A partial listing of materials known to catalyze alkylation of aromatics, which is not intended to be comprehensive of all the catalytic materials utilizable herein, would include: AlCl$_3$; AlCl$_3$.HCl; AlCl$_3$.H$_2$O; AlBr$_3$; FeCl$_3$; SnCl$_4$; TiCl$_4$; ZrCl$_4$; BF$_3$-Et$_2$O; PF$_5$; H$_2$SO$_4$; CH$_3$SO$_3$H; Amberlyst-15 (ion exchange resin); P$_2$O$_5$; H$_3$PO$_4$/kieselguhr; SiO$_2$.Al$_2$O$_3$; BF$_3$.Al$_2$O$_3$; EtAlCl$_2$.H$_2$O; and so forth. A more complete exposition of alkylation catalysts utilizable in the alkylation step of the hereindisclosed process, along with discussion of suitable reaction parameters for each, may be found in the treatise by G. A. Olah entitled *Friedel-Crafts and Related Reactions*, Vol. II (published by Interscience, 1963). Broadly speaking, such catalysts will promote the alkylation reaction at temperatures ranging from about minus 50° C. to about plus 200° C. and pressures of from about 5×10$^{-4}$ N/m$^2$ to about 10$^6$ N/m$^2$ (0.5-10 atm.) and greater. Preferred reaction conditions include temperatures of between about 0° C. and about 150° C. and ambient pressure.

In a particularly preferred embodiment, which embodiment is the subject of concurrently filed U.S. Patent Application Ser. No. 969,629, the alkylation catalyst utilized herein comprises a specific and novel type crystalline zeolite catalyst having unusual alkylation properties. Said zeolite catalyst is characterized by silica to alumina ratio of at least about 12 and a constraint index, as hereinafter more fully defined, of from about 1 to about 12. Contemplated appropriate reaction conditions include a zeolite catalyst bed temperature between approximately 100° C. and 400° C. and a pressure of from about 10$^5$ N/m$^2$ to about 4×10$^6$ N/m$^2$, although temperatures of between about 200° C. and 350° C. and operating pressures between about 10$^6$ and 3.5×10$^6$ N/m$^2$ are preferred. The reactants are most frequently passed across the catalyst, which comprises a bed of particulate material containing a crystalline zeolite catalyst as hereinafter defined, as a continuous stream at a feed weight hourly space velocity (WHSV) of between about 1 and about 100. The latter WHSV is based upon the weight of the catalyst compositions, i.e., the total weight of active catalyst and binder therefor. Contact between the reactants and the catalyst bed is preferably carried out at a WHSV of between about 5 and about 12.

Any or all of the component steps of the process of this invention may be carried out as a batch-type, semi-continuous or continuous operation utilizing a fixed, fluidized or moving bed catalyst system. A preferred embodiment entails use of a fluidized catalyst zone wherein the reactants are passed concurrently or countercurrently through a moving fluidized bed of the catalyst. The fluidized bed after use is conducted to a regeneration zone wherein coke is burned from the catalyst in an oxygen-containing atmosphere, e.g., air, at an elevated temperature, after which the regenerated catalyst is recycled to the conversion zone for further contact with the aromatic reactants.

The process may be carried out in a system wherein the reactants are in either the liquid or the vapor state, and the mixture of olefinic and aromatic compounds may be substantially pure (i.e., contain no substantial quantity of hydrocarbon material other than said mixture of said olefinic and aromatic materials) or may contain substantial amounts of other hydrocarbon materials. The latter situation is such as, for instance, would exist when some or all of the feed stream for the instant process also comprises the effluent stream of an earlier upstream process, for instance a process for the commercial manufacture of olefinic or aromatic compounds. Also, the feed stream for the process of this invention may contain other inert materials as diluents or solvents. Suitable diluents include, but are not limited to: hydrogen, carbon dioxide, methane, ethane, propane, cyclohexane, etc.

The crystalline zeolites utilized herein are members of a novel class of zeolites which exhibits unusual properties. Although these zeolites have unusually low alumina contents, i.e., high silica to alumina ratios, they are very active even when the silica to alumina ratio exceeds 30. The activity is surprising since catalytic activity is generally attributed to framework aluminum atoms and/or cations associated with these aluminum atoms. These zeolites retain their crystallinity for long periods in spite of the presence of steam at high temperature which induces irreversible collapse of the framework of other zeolites, e.g., of the X and A type. Furthermore, carbonaceous deposits, when formed, may be removed by controlled burning at higher than usual temperatures to restore activity. These zeolites, used as catalysts, generally have low coke-forming activity and therefore are conductive to long times on stream between regenerations by burning with oxygen-containing gas such as air.

An important characteristic of the crystal structure of this class of zeolites is that it provides constrained access to and egress from the intracrystalline free space by virtue of having an effective pore size intermediate between the small pore Linde A and the large pore Linde X, i.e., the pore windows of the structure have about a size such as would be provided by 10-membered rings of silicon and aluminum atoms interconnected by oxygen atoms. It is to be understood, of course, that these rings are those formed by the regular disposition of the tetrahedra making up the anionic framework of the crystalline zeolite, the oxygen atoms themselves being bonded to the silicon or aluminum atoms at the centers of the tetrahedra. Briefly, the preferred type zeolites useful in this invention possess, in combination: a silica to alumina mole ratio of at least about 12 and a structure providing constrained access to the intracrystalline free space.

The silica to alumina ratio referred to may be determined by conventional analysis. This ratio is meant to represent, as closely as possible, the ratio in the rigid anionic framework of the zeolite crystal and to exclude aluminum in the binder or in cationic or other form within the channels. Although zeolites with a silica to alumina ratio of at least 12 are useful, it is preferred to use zeolites having higher ratios of at least about 30. Such zeolites, after activation, acquire an intracrystalline sorption capacity for normal hexane which is greater than that for water, i.e., they exhibit "hydrophobic" properties. It is believed that this hydrophobic character is advantageous in the present invention.

The zeolites useful in this invention have an effective pore size such as to freely sorb normal hexane. In addition, the structure must provide constrained access to larger molecules. It is sometimes possible to judge from a known crystal structure whether such constrained access exists. For example, if the only pore windows in a crystal are formed by 8-membered rings of silicon and aluminum atoms, then access by molecules of larger cross-section than hexane is excluded and the zeolite is not of the desired type. Windows of 10-membered rings are preferred, although in some instances excess puckering of the rings or pore blockage may render these zeolites ineffective. Although it is thought that twelve-membered rings usually do not offer sufficient constraint to produce advantageous conversions, it is noted that the puckered 12-ring structure of TMA offretite shows constrained access. Other 12-ring structure may exist which may be operative and it is not the intention to judge the usefulness herein of a particular zeolite merely from theoretical structural considerations.

Rather than attempt to judge from crystal structure whether or not a zeolite possesses the necessary constrained access to molecules larger than normal paraffins, a simple determination of the "Constraint Index", as herein defined, may be made by passing continuously a mixture of an equal weight of hexane and 3-methylpentane over a small sample, approximately one gram or less, of the zeolite at atmospheric pressure according to the following procedure. A sample or the zeolite, in the form of pellets of extrudate, is crushed to a particle size about that of coarse sand and mounted in a glass tube. Prior to testing, the zeolite is treated with a stream of air at 540° C. for at least 15 minutes. The zeolite is then flushed with helium and the temperature adjusted between 290° C. and 510° C. to give an overall conversion between 10% and 60%. The mixture of hydrocarbons is passed at 1 liquid hourly space velocity (i.e., 1 volume of liquid hydrocarbon per volume of zeolite per hour) over the zeolite with a helium dilution to give a helium to total hydrocarbon mole ratio of 4:1. After 20 minutes on stream, a sample of the effluent is taken and analyzed, most conveniently by gas chromatography, to determine the fraction remaining unchanged for each of the two hydrocarbons.

The "Contsraint Index" is calculated as follows:

$$\text{Constraint Index} = \frac{\log_{10}(\text{fraction of hexane remaining})}{\log_{10}(\text{fraction of 3-methylpentane remaining})}$$

The Constraint Index approximates the ratio of the cracking rate constants for the two hydrocarbons. Zeolites suitable for the present invention are those having a Constraint Index of 1 to 12. Constraint Index (CI) values for some typical zeolites are:

| Zeolite | C.I. |
|---|---|
| ZSM-5 | 8.3 |
| ZSM-11 | 8.7 |
| ZSM-12 | 2 |
| ZSM-23 | 9.1 |
| ZSM-35 | 4.5 |
| ZSM-38 | 2 |
| TMA Offretite | 3.7 |
| Beta | 0.6 |
| ZSM-4 | 0.5 |
| H-Zeolon (mordenite) | 0.4 |
| REY | 0.4 |
| Amorphous Silica-Alumina | 0.6 |
| Erionite | 38 |

The above-described Constraint Index is an important and even critical definition of those zeolites which are useful in the instant invention. The very nature of this parameter and the recited technique by which it is determined, however, admit of the possibility that a given zeolite can be tested under somewhat different conditions and thereby have different Constraint Indices. Constraint Index seems to vary somewhat with severity of operation (conversion) and the presence or absence of binders. Therefore, it will be appreciated that it may be possible to so select test conditions to establish more than one value in the range of 1 to 12 for the Constraint Index of a particular zeolite. Such a zeolite exhibits the constrained access as herein defined and is to be regarded as having a Constraint Index of 1 to 12. Also contemplated herein as having a Constraint Index of 1 to 12 and therefore within the scope of the novel class of highly siliceous zeolites are those zeolites which, when tested under two or more sets of conditions within the above specified ranges of temperature and conversion, produce a value of the Constraint Index slightly less than 1, e.g., 0.9, or somewhat greater than 12, e.g., 14 or 15, with at least one other value of 1 to 12. Thus, it should be understood that the Constraint Index value as used herein is an inclusive rather than an exclusive value. That is, a zeolite when tested by any combination of conditions within the testing definition set forth hereinabove to have a Constraint Index of 1 to 12 is intended to be included in the instant catalyst definition regardless that the same identical zeolite tested under other defined conditions may give a Constraint Index value outside of the 1 to 12 range.

The class of zeolites defined herein is exemplified by ZSM-5, ZSM-11, ZSM-12, ZSM-23, ZSM-35, ZSM-38, and other similar materials. U.S. Pat. No. 3,702,886 describing and claiming ZSM-5 is incorporated herein by reference.

ZSM-11 is more particularly described in U.S. Pat. No. 3,709,979, the entire content of which is incorporaed herein by reference.

ZSM-12 is more particularly described in U.S. Pat. No. 3,832,449, the entire content of which is incorporated herein by reference.

ZSM-23 is more particularly described in U.S. Pat. No. 4,076,842, the entire content of which is incorporated herein by reference.

ZSM-35 is more particularly described in U.S. Pat. No. 4,016,245, the entire content of which is incorporated herein by reference.

ZSM-38 is more particularly described in U.S. Pat. No. 4,046,859, the entire content of which is incorporated herein by reference.

The specific zeolites described, when prepared in the presence of organic cations, are substantially catalytically inactive, possibly because the intracrystalline free space is occupied by organic cations from the forming solution. They may be activated by heating in an inert atmosphere at 540° C. for one hour, for example, followed by base exchange with ammonium salts followed by calcination at 540° C. in air. The presence of organic cations in the forming solution may not be absolutely essential to the formation of this type zeolite; however, the presence of these cations does appear to favor the formation of this special class of zeolite. More generally, it is desirable to activate this type catalyst by base exchange with ammonium salts followed by calcination in air at about 540° C. for from about 15 minutes to about 24 hours.

Natural zeolites may sometimes be converted to this type zeolite catalyst by various activation procedures and other treatments such as base exchange, steaming, alumina extraction and calcination, in combinations. Natural minerals which may be so treated include ferrierite, brewsterite, stilbite, dachiardite, epistilbite, heulandite, and clinoptilolite. The preferred crystalline zeolites are ZSM-5, ZSM-11, ZSM-12, ZSM-23, ZSM-35, and ZSM-38, with ZSM-5 and ZSM-12 being particularly preferred for the alkylation reaction of Step (1).

In a preferred aspect of this invention, the zeolites hereof are selected as those having a crystal framework density, in the dry hydrogen form, of not less than about 1.6 grams per cubic centimeter. It has been found that zeolites which satisfy all three of these criteria are most desired for several reasons. When hydrocarbon products or by-products are catalytically formed, for example, such zeolites tend to maximize the production of gasoline boiling range hydrocarbon products. Therefore, the preferred zeolites of this invention are those having a Constraint Index as defined above of about 1 to about 12, a silica to alumina ratio of at least about 12 and a dried crystal density of not less than about 1.6 grams per cubic centimeter. The dry density for known structures may be calculated from the number of silicon plus aluminum atoms per 1000 cubic Angstroms, as given, e.g., on Page 19 of the article on Zeolite Structure by W. M. Meier. This paper, the entire contents of which are incorporated herein by referene, is included in "Proceedings of the Conference on Molecular Sieves, London, April 1967", published by the Society of Chemical Industry, London, 1968.

When the crystal structure is unknown, the crystal framework density may be determined by classical pyknometer techniques. For example, it may be determined by immersing the dry hydrogen form of the zeolite is an organic solvent which is not sorbed by the crystal. Or, the crystal density may be determined by mercury porosimetry, since mercury will fill the interstices between crystals but will not penetrate the intracrystalline free space. It is possible that the unusual sustained activity and stability of the this class of zeolites is associated with its high crystal anionic framework density of not less than about 1.6 grams per cubic centimeter. This high density must necessarily be associated with a relatively small amount of free space within the crystal, which might be expected to result in more stable structures. This free space, however, is important as the locus of catalytic activity.

Crystal framework densities of some typical zeolites, including some which are not within the purview of this invention, are:

| Zeolite | Void Volume | Framework Density |
|---|---|---|
| Ferrierite | 0.28 cc/cc | 1.76 g/cc |
| Mordenite | .28 | 1.7 |
| ZSM-5, -11 | .29 | 1.79 |
| ZSM-12 | | 1.8 |
| ZSM-23 | | 2.0 |
| Dachiardite | .32 | 1.72 |
| L | .32 | 1.61 |
| Clinoptilolite | .34 | 1.71 |
| Laumontite | .34 | 1.77 |
| ZSM-4 (Omega) | .38 | 1.65 |
| Heulandite | .39 | 1.69 |
| P | .41 | 1.57 |
| Offretite | .40 | 1.55 |
| Levynite | .40 | 1.54 |
| Erionite | .35 | 1.51 |
| Gmelinite | .44 | 1.46 |
| Chabazite | .47 | 1.45 |
| A | .5 | 1.3 |
| Y | .48 | 1.27 |

When synthesized in the alkali metal form, the zeolite is conveniently converted to the hydrogen form, generally by intermediate formation of the ammonium form as a result of ammonium exchange and calcination of the ammonium form to yield the hydrogen form. In addition to the hydrogen form, other forms of the zeolite wherein the original alkali metal has been reduced to less than about 1.5 percent by weight may be used. Thus, the original alkali metal of the zeolite may be replaced by ion exchange with other suitable ions of Groups IB to VIII of the Periodic Table, including, by way of example, nickel, copper, zinc, palladium, calcium or rare earth metals.

In practicing the desired conversion process, it may be desirable to incorporate the above described crystalline zeolite in another material resistant to the temperature and other conditions employed in the process. Such matrix materials include synthetic or naturally occurring substances as well as inorganic materials such as clay, silica and/or metal oxides. The latter may be either naturally occurring or in the form of gelatinous precipitates or gels including mixtures of silica and metal oxides. Naturally occurring clays which can be composited with the zeolite include those of the montmorillonite and kaolin families, which families include the sub-bentonites and the kaolins commonly known as Dixie, McNamee-Georgia and Florida clays or others in which the main mineral constituent is halloysite, kaolinite, dickite, nacrite or anauxite. Such clays can be used in the raw state as originally mined or initially subjected to calcination, acid treatment or chemical modification.

In addition to the foregoing materials, the zeolites employed herein may be composited with a porous matrix material, such as alumina, silica-alumina, silica-magnesia, silica-zirconia, silica-thoria, silica-berylia, silica-titania as well as ternary compositions, such as silica-alumina-thoria, silica-alumina-zirconia, silica-alumina-magnesia and silica-magnesia-zirconia. The matrix may be in the form of a cogel. The relative proportions of zeolite component and inorganic oxide gel matrix on an anhydrous basis may vary widely with the zeolite content ranging from between about 1 to about 99 percent by weight and more usually in the range of about 5 to about 80 percent by weight of the dry composite.

The starting material in the Step (1) (alkylation) reaction comprises any of a number of monoalkylbenzenes. The choice of precisely which monoalkylbenzene compound to use as starting material is determined primarily by the desired end-product. For instance: if one wishes to produce 3-methylphenol (m-cresol), the appropriate starting material would be methylbenzene (toluene), while ethylbenzene would ultimately produce 3-ethylphenol. Any monoalkylbenzene compound, whrein the alkyl substituent comprises a hydrocarbon compound having from 1 to 20 carbon atoms, is suitable for the purposes of the present process, although for the manufacture of 3-alkylphenols the most preferred alkyl substituents are those having from 1 to 7 carbon atoms. As a general proposition, the following relationships of alkyl substituents on the benzene ring will be of value in choosing appropriate reactants for the present process: relative ease of dealkylation: (Step 2)

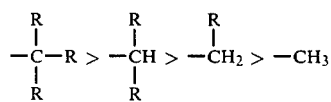

relative ease of oxidation: (Step 3)

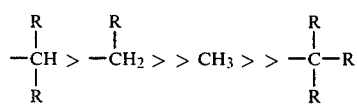

Applying these relationships to the manufacture of an exemplary 3-alkylphenol, e.g. 3-methylphenol, it can be seen that a preferred combination of starting materials might be methyl benzene and propylene to give a product of the Step (1)-alkylation reaction comprising:

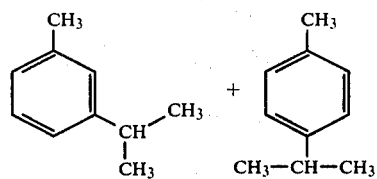

Using the above relationships, it will be clear that the methyl group will remain firmly fixed (i.e. will not dealkylate or oxidize) during the subsequent process steps except under the most severe of conditions. During the Step (2) reaction, which is more fully described hereinafter, the para-isopropyl group will crack off of the ring relatively easily while the meta-isopropyl group will remain and be easily and selectively oxidized to the hydroperoxide (Step (3)).

Monalkyl benzenes having larger primary or secondary alkyl substituents, i.e. those comprising from about 3 to about 5 carbon atoms, are particularly suitable for the production of 1,3-dihydroxybenzene (resorcinol; 1,3-benzenediol), which is another embodiment of the process hereindisclosed. These larger primary or secondary alkyl substituents are more easily oxidized in the later stages of the instant process (i.e. Steps (3) and (4)) than are the smaller alkyl groups, although it should be borne in mind that any alkyl substituent, regardless of its size, can be oxidized by the reaction of Steps (3) and (4) if the reaction conditions are of sufficient severity and the reaction permitted to proceed long enough. If the desired end product is to comprise 1,3-dihydroxybenzene, the most preferred starting material would be isopropylbenzene, which is then alkylated to produce diisopropylbenzene for subsequent oxidation to the desired dihydroxy compound. Similarly, if one wishes to start with benzene, the operating parameters of Step (1) may then be appropriately manipulated to produce the dialkyl adduct (e.g. diisopropylbenzene) which will subsequently yield the desired 1,3-dihydroxybenzene.

The olefinic component, which comprises the alkylating agent of the reaction mixture of Step (1), may be any unsaturated hydrocarbon having from 2 to about 20 carbon atoms and at least one olefinic linkage (i.e. carbon-carbon double bond) in the molecule. The double bond may be terminal, i.e. between a terminal carbon atom and the next adjacent carbon in the molecule, or it may be internal, i.e. between two adjacent non-terminal carbon atoms. Suitable alkylating agents include, but are not limited to: ethylene, propylene, butene (any isomer), pentene (any isomer), and cyclohexene. Also, compounds which will, in the presence of the alkylation catalysts defined herein, generate molecules having unsaturated carbon atoms suitable for the alkylation reaction are usable in the instant process. Such compounds capable of generating unsaturated carbon include, for example: methanol, ethanol, isopropyl alcohol, isopropyl ether, cyclohexyl chloride, and so forth.

Step 2—Selective Cracking

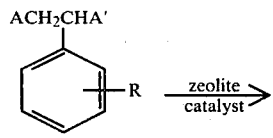

-continued

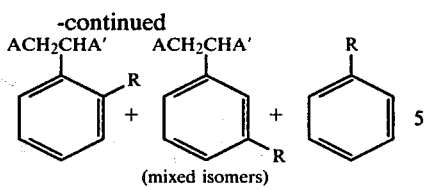

(mixed isomers)

where
R=alkyl
A=hydrogen or alkyl
A'=hydrogen or alkyl

Step (2) of the process comprises, in substance, contacting the reaction product of Step (1) with a particular crystalline zeolite catalyst, as herein defined, under suitable conversion or transalkylation conditions so as to selectively react (and thereby remove) the undesirable 1,4-isomer of the alkylated aromatic compound. As in Step (1), the instant reaction may be carried out in any of a number of physical process configurations, but the preferred embodiment comprises conducting the reaction in a fixed bed catalyst zone.

As hereinafter applied, the term "suitable conversion or transalkylation conditions" is meant to describe those conditions of temperature, pressure and duration of contact between the reactants and zeolitic catalyst which will result in the selective reaction of 1,4-isomer of the alkylated aromatic constituent of the reaction feed mixture, in general (but not necessarily exclusive) preference to the 1,2-isomer or the 1,3-isomer thereof. It is contemplated that such conditions shall include a catalyst bed temperature of between approximately 100° C. and 500° C., operating pressures of from about $10^4$ N/m$^2$ to about $10^6$ N/m$^2$ (about 0.1 to 10 atmospheres) and WHSV of about 0.1 hr$^{-1}$ to about 50 hr$^{-1}$. Preferred conditions include a temperature of from about 300° C. to about 450° C., pressure between about $5 \times 10^4$ N/m$^2$ to $5 \times 10^5$ N/m$^2$ (0.5 to 5 atmospheres) and WHSV of about 0.5 hr$^{-1}$ to 5 hr$^{-1}$.

The crystalline zeolite catalysts of Step (2) are the same as those defined previously in regard to Step (1) and, as in Step (1), the preferred catalysts include those designated as ZSM-5, ZSM-11, ZSM-12, ZSM-23, ZSM-35 and ZSM-38. The crystalline zeolites ZSM-5, ZSM-11 and ZSM-23 are particularly preferred for the reaction of Step (2).

In addition, for the purposes of Step (2), the crystalline zeolites employed may be modified prior to use by combining therewith a small amount, generally in the range of about 0.5 to about 40 percent, of a preferably difficultly reducible oxide, such as the oxides of phosphorus, boron, magnesium or combinations thereof and also oxides of antimony. Modifications of the zeolite with the desired oxide or oxides can readily be effected by contacting the zeolite with a solution of an appropriate compound of the element to be introduced, followed by drying and calcining to convert the compound to its oxide form.

Representative phosphorus-containing compounds which may be used include derivatives of groups represented by $PX_3$, $RPX_2$, $R_2PX$, $R_3P$, $X_3PO$, $(XO)_3PO$, $(XO)_3P$, $R_3P=O$, $R_3P=S$, $RPO_2$, $RP(O)(OX)_2$, $RP(S)(SX)_2$, $R_2P(O)OX$, $R_2P(S)SX$, $RP(OX)_2$, $ROP(OX)_2$, $RSP(SX)_2$, $(RS)_2PSP(SR)_2$, and $(RO)_2POP(OR)_2$, where R is an alkyl or aryl, such as a phenyl radical and X is hydrogen, R, or halide. These compounds include primary, $RPH_2$, secondary, $R_2PH$ and tertiary, $R_3P$, phosphines such as butyl phosphine; the tertiary phosphine oxides $R_3PO$, such as tributylphosphine oxide, th tertiary phosphine sulfides, $R_3PS$, the primary, $RP(O)(OX)_2$, and secondary, $R_2P(O)OX$, phosphonic acids such as benzene phosphonic acid; the corresponding sulfur derivatives such as $RP(S)(SX)_2$ and $R_2P(S)SX$, the esters of the phosphonic acid such as diethyl phosphonate, $(RO)_2P(O)H$, dialkyl alkyl phosphonates, $(RO)_2P(O)R$, and alkyl dialkylphosphinates, $(RO)P(O)R_2$; phosphinous acids, $R_2POX$, such as diethylphosphinous acid, primary, $(RO)P(OX)_2$, secondary, $(RO)_2POX$, and tertiary; $(RO)_3P$, phosphites; and esters thereof such as the monopropyl ester, alkyl dialkylphosphonites, $(RO)PR_2$, and dialkyl alkylphosphinite, $(RO)_2PR$ esters. Corresponding sulfur derivatives may also be employed including $(RS)_2P(S)H$, $(RS)_2P(S)R$, $(RS)P(S)R_2$, $R_2PSX$, $(RS)P(SX)_2$, $(RS)_2PSX$, $(RS)_3P$, $(RS)PR_2$ and $(RS)_2PR$. Examples of phosphite esters include trimethylphosphite, triethylphosphite, diisopropylphosphite, butylphosphite; and pyrophosphites such as tetraethylpryrophosphite. The alkyl groups in the mentioned compounds contain one to four carbon atoms.

Other suitable phosphorus-containing compounds include the phosphorus halides such as phosphorus trichloride, bromide, and iodide, alkyl phosphorodichloridites, $(RO)PCl_2$, dialkyl phosphorochloridites, $(RO)_2PX$, dialkylphosphinochloridites, $R_2PCl$, alkyl alkylphosphonochloridates, $(RO)(R)P(O)Cl$, dialkyl phosphinochloridates, $R_2P(O)Cl$ and $RP(O)Cl_2$. Applicable corresponding sulfur derivatives include $(RS)PCl_2$, $(RS)_2PX$, $(RS)(R)P(S)Cl$ and $R_2P(S)Cl$.

Preferred phosphorus-containing compounds include diphenyl phosphine chloride, trimethylphosphite and phosphorus trichloride, phosphoric acid, phenyl phosphine oxychloride, trimethylphosphite, diphenyl phosphinous acid, diphenyl phosphinic acid, diethylchlorothiophosphate, methyl acid phosphate and other alcohol-$P_2O_5$ reaction products.

Reaction of the zeolite with the phosphorus compound is effected by contacting the zeolite with such compound. Where the treating phosphorus compound is a liquid, such compound can be in solution in a solvent at the time contact with the zeolite is effected. Any solvent relatively inert with respect to the treating compound and the zeolite may be employed. Suitable solvents include water and aliphatic, aromatic or alcoholic liquids. Where the phosphorus-containing compound is, for example, trimethylphosphite or liquid phosphorus trichloride, a hydrocarbon solvent such as octane may be employed. The phosphorus-containing compound may be used without a solvent, i.e., may be used as a neat liquid. Where the phosphorus-containing compound is in the gaseous phase, such as where gaseous phosphorus trichloride is employed, the treating compound can be used by itself or can be used by itself or can be used in admixture with a gaseous diluent relatively inert to the phosphorus-containing compound and the zeolite, such as air or nitrogen, or with an organic solvent, such as octane or toluene.

Prior to reacting the zeolite with the phosphorus-containing compound, the zeolite may be dried. Drying can effected in the presence of air. Elevated temperatures may be employed. However, the temperature should not be such that the crystal structure of the zeolite is destroyed.

Heating of the phosphorus-containing catalyst subsequent to preparation and prior to use is also preferred.

The heating can be carried out in the presence of oxygen for example, air. Heating can be at a temperature of about 150° C. However, higher temperatures, e.g., up to about 500° C., are preferred. Heating is generally carried out for 3–5 hours but may be extended to 24 hours or longer. While heating temperatures above about 500° C. can be employed, they are generally not necessary. At temperatures of about 1000° C. the crystal structure of the zeolite tends to deteriorate.

The amount of phosphorus incorporated with the zeolite should be at least about 0.25 percent by weight. However, it is preferred that the amount of phosphorus in the zeolite be at least about 1 percent by weight when the same is combined with a finder, e.g. 35 weight percent of alumina. The amount of phosphorus can be as high as about 25 percent by weight or more depending on the amount and type of binder present. Preferably, the amount of phosphorus added to the zeolite is between about 0.5 and about 15 percent by weight.

The amount of phosphorus incorporated with the zeolite by reaction with elemental phosphorus of phosphorus-containing compound will depend upon several factors. One of these is the reaction time, i.e., the time that the zeolite and the phosphorus-containing source are maintained in contact with each other. With greater reaction times, all other factors being equal, a greater amount of phosphorus is incorporated with the zeolite. Other factors upon which the amount of phosphorus incorporated with the zeolite is dependent include reaction temperature, concentration of the treating compound in the reaction mixture, the degree to which the zeolite has been dried prior to reaction with the phosphorus-containing compound, the conditions of drying of the zeolite after reaction of the zeolite with the treating compound, and the amount and type of binder incorporated with the zeolite.

Another suitable modifying oxide is that of magnesium. Representative magnesium-containing compounds include magnesium acetate, magnesium nitrate, magnesium benzoate, magnesium propionate, magnesium 2-ethylhexoate, magnesium carbonate, magnesium formate, magnesium oxylate, magnesium amide, magnesium bromide, magnesium hydride, magnesium lactate, magnesium laurate, magnesium oleate, magnesium palmitate, magnesium salicylate, magnesium stearate and magnesium sulfide.

Reaction of the zeolite with the treating magnesium compound is effected by contacting the zeolite with such compound. Where the treating compound is a liquid, such compound can be in solution in a solvent at the time contact with the zeolite is effected. Any solvent relatively inert with respect to the treating magnesium compound and the zeolite may be employed. Suitable solvents include water and aliphatic, aromatic or alcoholic liquid. The treating compound may also be used without a solvent, i.e. may be used as a neat liquid. Where the treating compound is in the gaseous phase, it can be used by itself or can be used in admixture with a gaseous diluent relatively inert to the treating compound and the zeolite such as helium or nitrogen, or with an organic solvent such as octane or toluene.

Heating of the magnesium compound impregnated catalyst subsequent to preparation and prior to use is preferred. The heating can be carried out in the presence of oxygen, for example, air. Heating can be at a temperature of about 150° C. However, higher temperatures, e.g. up to about 500° C., are preferred. Heating is generally carried out for 1–5 hours but may be extended to 24 hours or longer. While heating temperatures above about 500° C. may be employed, they are generally not necessary. At temperatures of about 1000° C. the crystal structure of the zeolite tends to deteriorate. After heating in air at elevated temperatures, the oxide form of magnesium is present.

The amount of magnesium oxide incorporated in the zeolite should be at least about 0.25 percent by weight. However, it is preferred that the amount of magnesium oxide in the zeolite be at least about 1 percent by weight, particularly when the same is combined with a binder, e.g. 35 weight percent of alumina. The amount of magnesium oxide can be as high as about 25 percent by weight or more depending on the amount and type of binder present. Preferably, the amount of magnesium oxide added to the zeolite is between about 0.5 and about 15 percent by weight.

Boron oxide is also an effective modifying component. Representative boron-containing compounds include boric acid, trimethylborate, boron hydride, boron oxide, boron sulfide, butylboron dimethoxide, butylboronic acid, dimethylboric anhydride, hexamethylborazine, phenylboric acid, triethylborane, tetramethylammonium borohydride, triphenyl boron, and allylborate.

Reaction of the zeolite with the boron compound is effected by contacting the zeolite with such compound. Where the treating boron compound is a liquid, such compound can be in solution in a solvent at the time contact with the zeolite is effected. Any solvent relatively inert with respect to the treating compound and the zeolite may be employed. Suitable solvents include water and aliphatic, aromatic or alcoholic liquids. Where the boron containing compound is, for example, trimethylborate, a hydrocarbon solvent such as octane may be employed. The boron-containing compound may be used without a solvent, i.e., may be used as a neat liquid. Where the boron-containing compound is in the gaseous phase, such as where gaseous diborane is employed, the treating compound can be used by itself or can be used in admixture with a gaseous diluent inert to the boron-containing compound and the zeolite, such as nitrogen or helium, or with an organic solvent, such as octane.

Prior to reacting the zeolite with the boron-containing compound, the zeolite may be dried. Drying can be effected in the presence of air. Elevated temperatures may be employed. However, the temperature should not be such that the crystal structure of the zeolite is destroyed.

Heating of the boron-containing catalyst subsequent to preparation and prior to use is also preferred. The heating can be carried out in the presence of oxygen, for example, air. Heating can be at a temperature of about 150° C. However, higher temperatures. e.g., up to about 500° C., are preferred. Heating is generally carried out for 3–5 hours but may be extended to 24 hours or longer. While heating temperatures above about 500° C. can be employed, they are generally not necessary. At temperatures of about 1000° C. the crystal structure of the zeolite tends to deteriorate.

The amount of boron incorporated with the zeolite should be at least about 0.25 percent by weight. However, it is preferred that the amount of boron in the zeolite be at least about 1 percent by weight when the same is combined with a binder, e.g. 35 weight percent of alumina. The amount of boron can be as high as about 20 percent by weight or more depending on the amount and type of binder present. Preferably, the amount of boron added to the zeolite is between about 1.5 and 10 percent by weight. Without being limited by any theoretical considerations, it is contemplated that boron is actually present in the zeolite in an oxidized state, such as $B_2O_3$.

Antimony oxide may also be employed as a modifying component. The antimony oxide is present as $Sb_2O_3$ alone or in admixture with other antimony oxides with or without metallic antimony or other antimony compounds being present. In all instances, regardless of the particular state of oxidation of the antimony, its content with respect to the zeolite is computed as if it were present as $Sb_2O_3$. Generally the amount of $Sb_2O_3$ in the composite catalyst will be between about 6 and about 40 weight percent and preferably between about 10 and about 35 weight percent. Antimony derivatives which may be used include: the hydride $SbH_3$; the halides $SbX_3$, $SbX_5$ (X=F, Cl, Br, I); organic alkyl and aryl stibines and their oxides $R_3Sb$, $R_5Sb$, $R_xSb=O$ (R=alkyl or aryl); halogen derivatives $RSbX_2$, $R_2SbX$, $RSbX_4$, $R_2SbX_3$, $R_3SbX_2$, $R_4SbX$; the acids $H_3SbO_3$, $HSbO_2$, $HSb(OH)_6$; organic acids such as $RSbO(OH)_2$, $R_2SbO\cdot OH$, all with R and X defined as above noted. Also included are organic ethers such as $R_2SbOSbR_2$; esters and alcoholates such as $Sb(OOCCH_3)_3$, $Sb(OC_4H_9)_3$, $Sb(OC_2H_5)_3$; and antimonyl salts as $(SbO)SO_4$, $(SbO)NO_3$, $K(SbO)C_4H_4O_6$, $NaSbO_2\cdot 3H_2O$.

In some instances, it may be desirable to modify the crystalline zeolite by combining therewith two or more of the specified oxides. Thus, the zeolite may be modified by prior combination therewith of oxides of phosphorus and boron, oxides of phosphorus and magnesium or oxides of magnesium and boron. When such modification technique is employed, the oxides may be deposited on the zeolite either sequentially or from a solution containing suitable compounds of the elements, the oxides of which are to be combined with the zeolite. The amounts of oxides present in such instance are in the same range as specified above for the individual oxides, with the overall added oxide content being between 0.5 and about 40 weight percent.

Still another modifying treatment entails steaming of the zeolite by contact with an atmosphere containing from about 5 about 100 percent steam at a temperature of from about 250° to about 1000° C. for a period of between about 0.25 and about 100 hours and under pressures ranging from sub-atmospheric to several hundred atmospheres to reduce the alpha value thereof to less than 500, and preferably less than 20, but greater than zero.

Another modifying treatment involves precoking of the catalyst to deposit a coating of between about 2 and about 75 and preferably between about 15 and about 75 weight percent of coke thereon. Precoking can be accomplished by contacting the catalyst with a hydrocarbon charge, e.g. toluene, under high severity conditions or alternatively at a reduced hydrogen to hydrocarbon concentration, i.e. 0 to 1 mole ratio of hydrogen to hydrocarbon, for a sufficient time to deposit the desired amount of coke thereon.

It is also contemplated that a combination of steaming and precoking of the catalyst under the above conditions may be employed to suitably modify the crystalline aluminosilicate zeolite catalyst.

Steps 3 and 4—Oxidation and Rearrangement

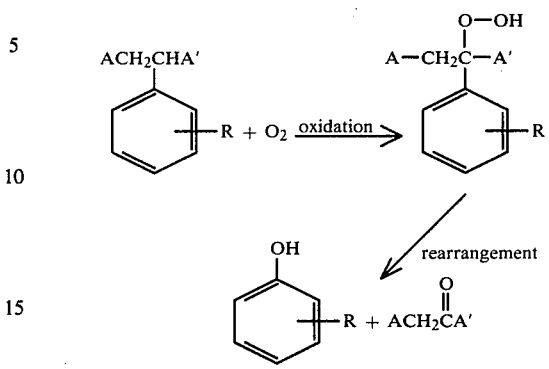

where:
R=alkyl
A=hydrogen or alkyl
A'=hydrogen or alkyl

The production of 3-alkylphenols and 1,3-dihydroxybenzene from the dialkylbenzene products of the above-described reactions is analogous to the well-known process for the manufacture of phenol from isopropylbenzene, i.e., oxidation of one or both of the alkyl substituents to the corresponding hydroperoxide (Step 3) followed by acid cleavage of the peroxide to yield the aromatic alcohol and a dialkyl ketone (Step 4).

Reaction conditions for oxidation and rearrangement are similar to conditions for the commercial isopropylbenzene/phenol process. The oxidation reaction may be conveniently carried out either in batch or continuous operation at 75° C. up to about 130° C. and at pressures ranging up to about $10^6$ N/M$^2$ (10 atm.). An appropriate base, preferably in aqueous solution, is used to maintain the pH of the reaction mixture at 7 to 9 to prevent decomposition of the hydroperoxide. It is also desirable to add a radical initiator to the reaction mix to optimize the conversion rate and selectivity to the desired hydroperoxide. Suitable radical initiators are well-known and the most preferable would be an organic hydroperoxide, particularly the same aromatic hydroperoxide which is the desired product of the reaction. However, numerous other conventional radical initiators may suitably be employed (e.g., metal oxide catalysts $MnO_2$). The source of oxygen for the formation of the hydroperoxide is normally an oxygen-containing gas (e.g., pure $O_2$ or air) which is brought into contact with the organic reactants by convenient means, such as continuous bubbling the gas through the reaction mixture under reaction conditions.

After formation of the hydroperoxide, it is cleaved and rearranged to the aromatic alcohol by bringing it into contact with an inorganic acid, such as $H_2SO_4$, preferably at elevated temperature. Alternatively, the hydroperoxide, in suitable solvent, may be converted to the aromatic alcohol by means of a cation exchange resin.

Prior to carrying out the rearrangement, it is preferable that the hydroperoxide be separated from the crude reaction product mix, thereby enabling one to maximize the efficiency of the cleavage reaction and also to recycle the unreacted starting materials to increase the yield and efficiency of the hydroperoxidation step. One suitable method of recovering the hydroperoxide would be by crystallization from the crude product mix, but the preferred method comprises extraction with an aqueous base (e.g., NaOH) followed by treatment of the salt with $CO_2$ to regenerate the hydroperoxide.

Recycling of the unreacted starting materials, particularly after extraction of the hydroperoxide product, is preferred, especially in continuous operations. However, such recycling may result in an accumulation of essentially inert by-products which will act as diluents and thereby prove detrimental to the reaction. It is therefore of benefit to minimize the accumulation of undesirable by-products by withdrawing a portion of the recycle prior to returning it to the oxidation reactor. Another method of preventing or minimizing accumulation of by-products would be to conduct the oxidation process in a cascade consisting of several reactors.

The following examples will serve to illustrate the process of this invention without placing undue limitations on the concept disclosed herein:

EXAMPLE 1

A mixture of toluene and ethylene was passed over microcrystalline HZSM-5 zeolite catalyst at 350° C. and atmospheric pressure. Two runs were made wherein the molar feed ratios of the toluene to ethylene were 5 and 7.6 respectively. Alkylation occurred to produce a mixture of ethyltoluene isomers as shown in Table I.

TABLE I

TOLUENE ALKYLATION WITH ETHYLENE

| Catalyst: microcrystalline HZSM-5 Temperature: 350° C. Pressure: atmospheric Conditions: | | |
|---|---|---|
| WHSV: Toluene | 7.0 | 10.5 |
| $C_2H_4$ | 0.4 | 0.4 |
| Molar Feed Ratio: | | |
| Toluene/$C_2H_4$ | 5 | 7.6 |
| Conversion, Wt. % | | |
| Toluene | 18.5 | 13.0 |
| $C_2H_4$ | 91.4 | 90.5 |
| Selectivity to products, wt.% | | |
| para-Ethyltoluene | 27.2 | 28.8 |
| meta-Ethyltoluene | 53.4 | 56.5 |
| ortho-Ethyltoluene | 13.4 | 12.0 |
| other aromatics | 4.7 | 1.2 |
| light gas | 1.3 | 1.5 |
| | 100.0 | 100.0 |

It is seen that, although the major product is the meta-isomer (b.p. 161.3° C.), substantial amounts of the para-isomer (b.p. 162.0° C.) have also been produced. It is evident that the close boiling points of these isomers would make it virtually impossible to make an acceptable separation by distillation. However, by selective cracking (i.e., Step 2), the para-isomer may be preferentially dealkylated (cracked) to produce toluene and light olefins leaving a mixture containing ortho and meta ethyltoluenes.

EXAMPLE 2

A sample of microcrystalline HZSM-5 was steamed for a period of 6 hours at 600° C. A mixture comprising ethylene and toluene was passed over the catalyst at 350° C. and atmospheric pressure, with WHSV of 6.96 (toluene) and 0.54 (ethylene). The products are summarized in Table II.

TABLE II

TOLUENE ALKYLATION WITH ETHYLENE

| Catalyst: microcrystalline HZSM-5, steamed for 6 hours at 600° C. Temperature: 350° C. Pressure: atmospheric Conditions | |
|---|---|
| WHSV: Toluene | 6.96 |
| $C_2H_4$ | 0.54 |
| Conversion, Wt. % | |
| Toluene | 11.1 |
| $C_2H_4$ | 74.6 |
| Selectivity to products, Wt. % | |
| para-Ethyltoluene | 40.3 |
| meta-Ethyltoluene | 58.8 |
| ortho-Ethyltoluene | 0 |
| Other aromatics | 0.5 |
| Light gas | 0.4 |
| | 100.0 |

The reaction produced primarily meta and para-ethyltoluenes. By steaming the catalyst, the production of the ortho-isomer was suppressed to below the detection level (i.e., <0.1%). By selective cracking, it will be possible to now convert the para-isomer to its lower boiling fragments, thereby permitting a separation of substantially pure meta-ethyltoluene by a relatively simple distillation.

EXAMPLE 3

The alkylation of toluene with ethylene was carried out at 300° C. and atmospheric pressure over HZSM-12 zeolite catalyst. The reactants, at a mole ratio of toluene to ethylene of 7/1, were passed over the catalyst at a feed WHSV of 6. Approximately 60% of the ethylene was converted to alkylation product, with a 90% selectivity to ethyltoluene. The isomer distribution was 40% ortho-ethyltoluene, 38% meta-ethyltoluene and 22% para-ethyltoluene.

EXAMPLE 4

Using the HZSM-12 catalyst of Example 3, toluene was alkylated with propylene (mole ratio=7/1) at 250° C. and 500 psig. The feed WHSV was 6. Conversion of the alkylating agent (propylene) was in excess of 95 wt. % and the reaction was approximately 95% selective to isopropyltoluene. Isomer distribution was 6% ortho-isopropyltoluene, 62% meta-isopropyltoluene and 32% para-isopropyltoluene.

EXAMPLE 5

Again using HZSM-12 zeolite as the alkylation catalyst, toluene was reacted with a mixture of 1-butene and 2-butene at 200° C. The reaction was carried out at 300 psig and WHSV of 6, the reactants being at a mole ratio (toluene to butenes) of 7/1. At this temperature the butene conversion was greater than 95% to sec-butyltoluene, with isomer distribution being 40% meta and 60% para with no indication of the ortho isomer. This isomer ratio was reversed by increasing the reactor temperature to approximately 235° C.

EXAMPLE 6

Temperature effect on the reaction was studied by alkylating toluene with propylene at 200°, 230° and 260° C. over HZSM-12 zeolite catalyst. In all cases the pressure was 500 psig with a molar feed ratio of 6.25/1 toluene/propylene. The feed rate for toluene was WHSV 5.7 and for propylene with WHSV was 0.4.

The propylene conversion at 230°–240° C. averaged 90–95% during a five day run. The selectivity to isopropyltoluene was 95% throughout the temperature range. The effect of temperature on isomer distribution is see in Table III.

TABLE III

EFFECT OF TEMPERATURE ON TOLUENE-PROPYLENE ALKYLATION

| Temperature °C. | Isopropyltoluene Isomer Distribution | | |
|---|---|---|---|
| | Ortho | Meta | Para |
| 200 | 18.4 | 31.8 | 49.8 |
| 230 | 6.9 | 60.3 | 32.8 |
| 260 | 5.3 | 63.7 | 31.0 |

EXAMPLE 7

A mixture comprising ethylbenzene and ethylene (mole ratio=4/1) was passed over a microcrystalline HZSM-5 zeolite catalyst at 250° C. and at 350° C. The feed rates for each of the respective components of the feed stream were a WHSV of 7.2 for the ethylbenzene and 0.5 for the ethylene in both runs. An alkylation reaction took place to produce a mixture of diethylbenzene isomers as shown in Table IV.

TABLE IV

ALKYLATION OF ETHYLBENZENE WITH ETHYLENE

| Catalyst: microcrystalline HZSM-5 zeolite | | |
|---|---|---|
| Feed WHSV: | | |
| Ethylbenzene | 7.2 | |
| Ethylene | 0.5 | |
| Temperature, °C. | 250 | 300 |
| Conversion, Wt. % | | |
| Ethylbenzene | 20.3 | 31.0 |
| Ethylene | 85.7 | 81.2 |
| Selectivity to Products, Wt. % | | |
| ortho-Diethylbenzene | 3.3 | 2.4 |
| meta-Diethylbenzene | 46.7 | 56.1 |
| para-Diethylbenzene | 27.5 | 27.8 |
| Other aromatics | 17.9 | 13.4 |
| Light gas | 4.6 | 0.3 |

It is evident from the close boiling points of the ethylbenzene isomers (ortho 183.4° C.; meta 181.1° C.; para 183.8° C.) in the product stream that the conventional method of separation (i.e., fractional distillation) would not be practical. However, by selective cracking the para-isomer may be preferentially dealkylated to produce lower boiling components which will thereafter permit isolation of the remaining ortho and meta-isomers.

EXAMPLE 8

Ethylbenzene was alkylated with propylene with 90% selectivity to isopropyl ethylbenzene (41% para, 59% meta and ortho). The reaction was carried out at 200° C. and atmospheric pressure, with an ethylbenzene/propylene mole ratio of 7/1 and a feed WHSV of 11 over 4.6 grams of HZSM-12 catalyst. The conversion of the alkylating agent was in excess of 95%.

EXAMPLE 9

At 200° C. and atmospheric pressure, isopropylbenzene (cumene) was alkylated with propylene utilizing 4.6 grams of HZSM-12 catalyst. At a WHSV of 11 and a 7/1 mole ratio of isopropylbenzene/propylene, greater than 95% of the propylene was converted with 95% selectivity to diisopropylbenzene. The isomer distribution was 60% para- and 40% meta. Increasing the reactor temperature to 235° C. resulted in a reversal of the meta/para isomer ratio of 61/39. The ortho isomer was not found.

EXAMPLE 10

In another reaction, analogous to Examples 4 and 6, toluene was alkylated with propylene at 240° C. and 500 psig. The catalyst was HZSM-12 zeolite and the feed WHSV and the mole ratio (toluene/propylene) were 5.06/0.40 and 5.83/1, respectively.

The reaction resulted in a 15.9 mole % convesion of the toluene (theoretical maximum=17.2%) and a propylene conversion of 98.3–99.9 mole %. Selectivity to isopropyltoluene was 91.9% (based on toluene) with an isomer distribution of 5.3% ortho, 63.8% meta and 30.8% para.

Step (2)—Selective Cracking

EXAMPLE 11

An isometric mixture of isopropyltoluenes (mole ratio para/meta/ortho=0.45/1.00/0.06) was brought into contact with a ZSM-5 zeolite catalyst which had been prepared according to U.S. Pat. No. 3,702,886 and steamed for one hour at 600° C. The reactor was at 350° C. and ambient pressure and the feed WHSV for the respective isomers was 1.50/3.36/0.20. The material balance for the reactants and products is given in Table V.

TABLE V

EXAMPLE 11
SELECTIVE CRACKING OF ISOPROPYLTOLUENES

| Compound | Feed Stream Wt. % | Product Stream Wt. % |
|---|---|---|
| Benzene | 0 | <0.1 |
| Toluene | 0.1 | 21.3 |
| Dimethylbenzene | 0 | .2 |
| para-Isopropyltoluene | 29.6 | 0 |
| meta-Isopropyltoluene | 66.3 | 64.8 |
| ortho-Isopropyltoluene | 4.0 | 2.6 |
| Aromatic $C_{10+}$ | 0 | 1. |
| $CH_4$ | 0 | <0.1 |
| $C_2H_6$ | 0 | <0.1 |
| $C_2H_4$ | 0 | 1.0 |
| $C_3H_8$ | 0 | 0.8 |
| $C_3H_6$ | 0 | 4.2 |
| $C_4H_{10}$ | 0 | 1.0 |
| $C_4H_8$ | 0 | 2.0 |
| $C_5H_{12}$ | 0 | 0.9 |

From the data it can be seen that all of the para-isomer has been reacted to produce primarily toluene and olefins. The meta-isomer has remained substantially unreacted, with only 2.2% having been converted, while 36.5% of the ortho-isomer has been cracked.

EXAMPLE 12

A diisopropylbenzene (DIPB) mixture containing 68.9 wt. % meta isomer and 23.2 wt. % para isomer was passed over 4.0 grams of ZSM-5 zeolite catalyst in a quartz microreactor at a feed weight hourly space velocity (WHSV) of 4.3 hr$^{-1}$ and at temperatures of 300° C. to 400° C. The results are shown in Table VI.

TABLE VI
SELECTIVE CRACKING OF DIISOPROPYLBENZENES
Catalyst: ZSM-5 zeolite
Feed WHSV: 4.3

| | Feedstock | | | |
|---|---|---|---|---|
| Temperature, °C. | — | 300 | 350 | 400 |
| Composition, wt. % of aromatics | | | | |
| meta-DIPB | 68.9 | 73.0 | 73.0 | 72.0 |
| para-DIPB | 23.2 | 12.5 | 5.9 | 3.1 |
| Benzene | — | 5.2 | 9.4 | 11.7 |
| Toluene | — | 0.4 | 0.8 | 1.4 |
| $C_8$ | — | 0.8 | 1.5 | 2.3 |
| Isopropylbenzene | 0.5 | 2.6 | 1.8 | 1.3 |
| Others | 7.4 | 5.5 | 7.6 | 8.2 |
| % meta-in DIPB | 74.8 | 85.4 | 92.5 | 95.9 |

As can be seen, at 400° C. the aromatic effluent from the reactor contained 72.0 wt. % meta-DIPB and 3.1 wt. % para-DIPB. Thus the relative proportion of meta isomer in the DIPB has been increased from 74.8% to 95.9% by selective cracking of the para isomer, yielding benzene as the major cracking product.

EXAMPLE 13

A mixture containing 52.0% meta-ethyltoluene (ET), 47.5 wt. % para-ET and 0.5 wt. % ortho-ET was contacted with 4.0 grams of the Mg-P modified ZSM-5 catalyst in a flow microreactor at 400°–500° C. and WHSV of 0.9–6.2 $hr^{-1}$. The results are shown in Table VII.

TABLE VII
SELECTIVE CRACKING OF ETHYLTOLUENES
Catalyst: Mg-P-ZSM-5 zeolite

| | Feedstock | | | |
|---|---|---|---|---|
| Temprature, °C. | — | 400 | 450 | 500 |
| WHSV, $hr^{-1}$ | — | 0.9 | 2.8 | 6.2 |
| Composition, wt % of aromatics | | | | |
| Benzene | — | 3.1 | 2.0 | 1.5 |
| Toluene | — | 43.4 | 40.6 | 40.2 |
| Ethylbenzene | — | 3.3 | 1.8 | 0.8 |
| Diethylbenzenes | — | 5.6 | 3.2 | 2.3 |
| para-Ethyltoluene | 47.5 | 9.3 | 7.3 | 5.2 |
| meta-Ethyltoluene | 52.0 | 32.5 | 43.1 | 49.1 |
| ortho-Ethyltoluene | 0.5 | 1.1 | 1.0 | 0.9 |
| Higher boiling compounds | — | 1.7 | 1.0 | — |
| % meta in Ethyltoluene | 52.0 | 75.8 | 83.9 | 89.0 |

It is shown that the % meta isomer in ethyltoluene, at 500° C. and WHSV of 6.2 $hr^{-1}$, was increased from 52% in the original feed to 89% in the reactor effluent by selective cracking of the para isomer.

EXAMPLE 14

A mixture comprising 66.2 wt. % 1-isopropyl-3-methylbenzene (meta-cymene), 29.8 wt. % 1-isopropyl-4-methylbenzene (para-cymene), and 4.0 wt. % 1-isopropyl-2-methylbenzene (ortho-cymene) was contacted with 4 grams of HZSM-11 catalyst which had been steamed at 600° C. for 3 hours at atmospheric pressure. The results are summarized in Table VIII.

TABLE VIII
SELECTIVE CRACKING OF CYMENES
Catalyst: HZSM-11

| | Feedstock |  |
|---|---|---|
| Temprature, °C. | — | 310 |
| WHSV, $hr^{-1}$ | — | 4.3 |
| Composition, wt % | | |

TABLE VIII-continued
SELECTIVE CRACKING OF CYMENES
Catalyst: HZSM-11

| | Feedstock | |
|---|---|---|
| Toluene | — | 36.90 |
| ortho-Cymene | 4.0 | 4.53 |
| meta-Cymene | 66.2 | 39.27 |
| para-Cymene | 29.8 | 1.62 |
| Aromatic $C_{10}$ | — | 3.51 |
| Other aromatics | — | 5.07 |
| $C_2H_4$ | — | 0.93 |
| $C_3H_6$ | — | 1.68 |
| $C_4H_8$ | — | 4.46 |
| Other light gases | — | 2.28 |
| % meta in Cymene | 66.2 | 86.5 |

It is again seen from the above results that the para-isomer has been selectively reduced with corresponding enrichment of the ortho- and meta-isomers in the cymene product fraction.

EXAMPLE 15

A feedstock containing 68.13 wt % 1-isopropyl-3-methylbenzene (meta-cymene), 27.54 wt % 1-isopropyl-4-methylbenzene (para-cymene), and 4.25 wt % 1-isopropyl-2-methylbenzene (ortho-cymene) was passed through a catalyst bed of 1.0 gram of ZSM-23 zeolite catalyst in a flow reactor at 300°–400° C. and WHSV of 3.8 $hr^{-1}$. The products are shown in Table IX. In all runs, the meta isomer has been enriched relative to the ortho and para isomers.

TABLE IX
Selective Cracking of Cymenes
Catalyst: ZSM-23 zeolite
Feed WHSV: 3.8 $hr^{-1}$

| | Feedstock | | | |
|---|---|---|---|---|
| Temperature, °C. | — | 300 | 350 | 400 |
| Composition, mole % of aromatics | | | | |
| Toluene | — | 19.38 | 40.63 | 58.11 |
| Xylenes | — | — | — | 1.25 |
| ortho-Cymene | 4.25 | 4.27 | 2.82 | 1.60 |
| meta-Cymene | 68.13 | 64.78 | 53.84 | 36.53 |
| para-Cymene | 27.54 | 11.57 | 2.72 | 1.67 |
| n-Propyltoluene | — | — | — | 0.85 |
| % meta in Cymenes | 68.1 | 80.4 | 90.7 | 91.8 |

Step (3)—Oxidation

EXAMPLE 16

A isopropyltoluene mixture comprising 6% ortho-isopropyltoluene and 92% meta-isopropyltoluene (0% para-isomer and 2% other compounds) was prepared by selective cracking (Step 2) followed by distillation. Equal volumes of the freshly distilled isopropyltoluene and 2.5% aqueous $NaHCO_3$ were added to a one liter autoclave. Oxygen was bubbled through the reactor at 11 liters per hour, while the autoclave was maintained at 120°–125° C. and 100 psi. A sample was periodically withdrawn for analysis of hydroperoxide formation. When no initiator was added to the reaction mixture less than 3% meta-isopropyltoluene hydroperoxide was formed after 10 hours of oxidation. When a small amount of isopropylbenzene hydroperoxide (total weight 0.8%) was added as an initiator, oxidation took place smoothly. The change in composition of the recetion mixture with time is shown in Table X.

TABLE X

| Products from Oxidation of meta-Isopropyltoluene | | | |
|---|---|---|---|
| Reaction time: | 0 | 1 hr. | 5 hrs. |
| Product Composition, % | | | |
| meta-isopropyltoluene | 89.7 | 87.7 | 69.4 |
| ortho-isopropyltoluene | 5.8 | 6.3 | 5.6 |
| Other compounds in starting mixture | 3.1 | 3.2 | 2.7 |
| (α-methylstyrene, meta) | — | 0.2 | 2.0 |
| (α-methylstyrene, para) | — | 0.3 | 2.2 |
| Isopropylbenzene hydroperoxide | 0.8 | 0.7 | 0.3 |
| meta-Isopropyltoluene hydroperoxide | — | 1.1 | 15.2 |
| Other by-products | — | — | 1.7 |

As can be seen, the concentration of the ortho-isopropyltoluene remained substantially constant during the oxidation. After 5½ hours of oxidation conversion of meta-isopropyltoluene was 25% and selectivity to meta-isopropyltoluene hydroperoxide was 75%. This example demonstrates the selective oxidation of meta-isopropyltoluene in mixture containing both meta and ortho isomers.

Step (4)—Rearrangement

EXAMPLE 17

A 25 ml solution containing approximately 26% meta-isopropyltoluene hydroperoxide was prepared by oxidation of meta-isopropyltoluene (Example 16). To this solution 0.5 ml of concentrated $H_2SO_4$ was added dropwise to catalyze the rearrangement of the meta-isopropyltoluene to 3-methylphenol. The rection mixture was then heated to 65° C. for ½ hour. The product spectrum is shown in Table XI. As will be seen, the conversion of the meta hydroperoxide was complete. No ortho-isopropyltoluene was converted during the oxidation and rearrangement steps into 2-methylphenol.

TABLE XI

| Rearrangement of meta-Isopropyltoluene Hydroperoxide | | |
|---|---|---|
| | Composition, % | |
| | Starting Material | Product |
| Acetone | 0 | 9.1 |
| Light ends | 1.3 | 1.5 |
| meta-Isopropyltoluene | 47.2 | 43.7 |
| ortho-Isopropyltoluene | 5.6 | 4.8 |
| meta-Isopropyltoluene hydroperoxide | 26.0 | 0 |
| 3-Methylphenol | 0 | 14.4 |
| (α-methylstyrene, meta) | 4.4 | 4.3 |
| (α-methylstyrene, para) | 8.1 | 0 |
| (isopropenyl compound) | 0 | 3.8 |
| Others | 7.2 | 18.3 |

Having thus generally described the process of the present invention and set forth specific examples in support thereof, it is to be understood that no undue restrictions are to be imposed on the scope of the concept disclosed herein by reason of the illustrative examples.

What is claimed is:

1. A process for the manufacture of 3-methylphenol comprising:
   (A) alkylating toluene with an alkylating agent by contacting said toluene with said alkylating agent at a temperature of from about 100° C. to about 400° C. and a pressure of from about $10^5$ N/m² to about $4 \times 10^6$ N/m² in the presence of a zeolite alkylation catalyst, said zeolite catalyst being characterized by a silica to alumina ratio of at least 12 and a constraint index of about 1 to about 12 and said alkylating agent consisting essentially of an unsaturated hydrocarbon having from 2 to about 20 carbon atoms and at least one olefinic linkage or a compound which will, in the presence of said zeolite alkylation catalyst, generate molecules having unsaturated carbon atoms;
   (B) contacting the product of Step (A) at a temperature of from about 150° C. to about 800° C. and a pressure of between about $10^4$ N/m² and $10^7$ N/m², with a shape selective zeolite catalyst to selectively react the 4-alkyltoluene component thereof, the reaction mixture thereby becoming enriched with respect to the 3-alkyltoluene component thereof, said shape selective zeolite catalyst being characterized by a constraint index within the range of from about 1 to about 12 and a silica to alumina ratio of at least 12;
   (C) oxidizing the mixture produced in Step (B) to produce the hydroperoxide of said 3-alkyltoluene; and
   (D) rearranging said hydroperoxide of said 3-alkyltoluene, in the presence of an inorganic acid catalyst, or cation exchange resin to produce said 3-methylphenol.

2. The process of claim 1 wherein said alkylating agent is propylene.

3. The process of claim 1 said temperature in said alkylation Step (A) is between about 200° C. and about 350° C.

4. The process of claim 1 wherein said zeolite alkylation catalyst is ZSM-5.

5. The process of claim 1 wherein said zeolite alkylation catalyst is ZSM-12.

6. The process of claim 1 wherein the selective reaction of said 4-alkyltoluene in Step (B) is carried out at a temperature of from about 250° C. to about 550° C. and a pressure of from $2 \times 10^4$ N/m² to $2.5 \times 10^6$ N/m².

7. The process of claim 1 wherein said shape selective zeolite catalyst of Step (B) is ZSM-5.

8. The process of claim 1 wherein said shape selective zeolite catalyst of Step (B) is ZSM-11.

9. The process of claim 1 wherein said shape selective zeolite catalyst of Step (B) is ZSM-23.

10. The process of claim 1 wherein a free radical initiator is present in said oxidation Step (C) to promote the formation of said hydroperoxide.

11. The process of claim 10 wherein the reaction mixture of said oxidation step (C) is adjusted to a pH of between 7 and 9 by the addition of a base thereto.

12. The process of claim 11 wherein said oxidation reaction is carried out at a temperature of from about 75° C. to about 130° C. and a pressure of up to about $10^6$ N/m$^2$.

13. The process of claim 1 wherein the rearrangement Step (D) is carried out by adding an inorganic acid to the hydroperoxide-containing product of oxidation Step (C) and heating.

14. The process of claims 1, 7, 8 or 9 wherein said shape selective zeolite catalyst has undergone prior modification by combining therewith between about 0.5 and about 40 weight percent of at least one oxide selected from the group consisting of the oxides of phosphorus, antimony, boron and magnesium.

15. The process of claims 1, 7, 8 or 9 wherein said shape selective zeolite catalyst has undergone prior modification by steaming at a temperature between about 250° C. and about 1,000° C. for a period of between about 0.5 and about 100 hours.

16. The process of claim 1, 4, 5, 7, 8, or 9 wherein said zeolite catalyst is admixed with a binder therefor.

* * * * *

UNITED STATES PATENT AND TRADEMARK OFFICE
CERTIFICATE OF CORRECTION

PATENT NO. : 4,197,413  Page 1 of 2
DATED : April 8, 1980
INVENTOR(S) : WARREN W. KAEDING, MARGARET M. WU, LEWIS B. YOUNG, and GEORGE T. BURRESS It is certified that error appears in the above-identified patent and that said Letters Patent are hereby corrected as shown below:

Column 2, line 62, before "100°C", "bout" should read "about";

Column 5, line 11, "conductive" should be "conducive";

Column 6, line 6, before "extrudate", "of" should read "or";

Column 9, line 39, after "compound", "whrein" should be corrected to read "wherein";

Column 10, line 16, "meta" should be underlined - thus, _meta_;

Column 11, line 62, after "$RPO_2$" insert --$RPS_2$--;

Column 11, line 63, after "$RP(OX)_2$" insert --$RP(SX)_2$--;

Column 12, line 1, correct the spelling of "the";

Column 13, line 14, "finder" should be "binder";

Column 13, line 21, after "elemental phosphorus", "of" should read "or";

Column 15, line 28, after "$Sb(OC_2H_5)_3$, insert --$Sb(OCH_3)_3$--;

Column 19, line 7, "see" should be "seen".

UNITED STATES PATENT AND TRADEMARK OFFICE
CERTIFICATE OF CORRECTION

PATENT NO. : 4,197,413

DATED : April 8, 1980

INVENTOR(S) : WARREN W. KAEDING, MARGARET M. WU, LEWIS B. YOUNG, and GEORGE T. BURRESS It is certified that error appears in the above-identified patent and that said Letters Patent are hereby corrected as shown below:

Column 2, between lines 15 and 20, in the structural formula, "selective cracking" should be underlined;

Column 2, line 30, in the structural formula, "oxidation" should be underlined;

Column 2, between lines 35 and 40, in the structural formula, "rearrangement" should be underlined:

Signed and Sealed this

Twenty-ninth Day of July 1980

[SEAL]

Attest:

SIDNEY A. DIAMOND

Attesting Officer

Commissioner of Patents and Trademarks